(12) United States Patent
Wasserman

(10) Patent No.: US 11,759,410 B2
(45) Date of Patent: Sep. 19, 2023

(54) SILICONE COMPOSITION AND USES THEREOF

(71) Applicant: Wasserman Medic AB, Höllviken (SE)

(72) Inventor: Peter Wasserman, Höllviken (SE)

(73) Assignee: Wasserman Medic AB, Höllviken (SE)

( * ) Notice: Subject to any disclaimer, the term of this patent is extended or adjusted under 35 U.S.C. 154(b) by 6 days.

(21) Appl. No.: 16/802,184

(22) Filed: Feb. 26, 2020

(65) Prior Publication Data

US 2020/0276092 A1 Sep. 3, 2020

(51) Int. Cl.
| | |
|---|---|
| A61K 8/29 | (2006.01) |
| A61K 8/27 | (2006.01) |
| A61K 8/891 | (2006.01) |
| A61K 8/92 | (2006.01) |
| A61Q 17/04 | (2006.01) |

(52) U.S. Cl.
CPC ............ *A61K 8/29* (2013.01); *A61K 8/27* (2013.01); *A61K 8/891* (2013.01); *A61K 8/922* (2013.01); *A61Q 17/04* (2013.01)

(58) Field of Classification Search
None
See application file for complete search history.

(56) References Cited

U.S. PATENT DOCUMENTS

| 8,557,287 B2 | 10/2013 | Schleuning | |
|---|---|---|---|
| 2010/0322875 A1 | 12/2010 | Guilbaud | |
| 2017/0022327 A1* | 1/2017 | Bao | A61Q 15/00 |
| 2018/0303744 A1* | 10/2018 | Dörr | A61Q 1/02 |

FOREIGN PATENT DOCUMENTS

| EP | 2921157 A1 | 9/2015 |
|---|---|---|
| WO | WO-01/23011 A1 | 4/2001 |
| WO | WO-2007/114904 A2 | 10/2007 |
| WO | WO-2008/085360 A2 | 7/2008 |
| WO | WO-2009/046033 A2 | 4/2009 |
| WO | WO-2012/000674 A1 | 1/2012 |
| WO | WO-2015/149322 A1 | 10/2015 |
| WO | WO-2017/073755 A1 | 5/2017 |

OTHER PUBLICATIONS

Lourith et al., "Development of sunscreen products containing passion fruit seed extract", Brazilian Journal of Pharmaceutical Sciences, 53(1), 2017, p. 1. (Year: 2017).*
Mintel GNPD Record ID: 2286017, "Prism Essence Foundation" (2014).
Response to Written Opinion and Amended Claims dated Jun. 18, 2020 from related International Application No. PCT/EP2020/053870.
International Preliminary Report on Patentability dated Oct. 20, 2020 from related sInternational Application No. PCT/EP2020/053870.

* cited by examiner

*Primary Examiner* — Bethany P Barham
*Assistant Examiner* — Janet Joseph
(74) *Attorney, Agent, or Firm* — MARSHALL, GERSTEIN & BORUN LLP

(57) ABSTRACT

The present invention relates to a silicone composition comprising the three silicone compounds: stearyl dimethicone, a C30-45 alkyl methicone, and a caprylyl methicone. Said combination provides a unique effect in the treatment of scars, by increasing hydration of stratum corneum and thereby facilitates regulation of fibroblast production and reduction in collagen production, whereby treatment of skin injuries is obtained. Said composition can be applied as a thin transparent silicone film on a desired skin area, does not require any drying time, and has an improved adherence to the patient's skin, thereby improving patient compliance during treatment. Furthermore, said silicone composition can be provided with an SPF of 50 and a relatively high silicone concentration.

29 Claims, No Drawings

SILICONE COMPOSITION AND USES THEREOF

Priority is claimed to Swedish patent application 1950265-7, which is incorporated herein by reference in its entirety.

The present invention relates to a silicone composition comprising a combination of at least three silicone compounds. Said silicone composition is suitable for promoting the healing of skin wounds and/or for the prevention of scarring.

Significant skin wounds, e.g. caused by injury or surgery, frequently lead to scarring, which in some situation may result in a diminished sense of touch, loss of flexibility and loss of range of motion (where scars run across joints). Scarring also results in obvious cosmetic problems, particularly when the scar is located on visible areas, e.g. the face and hands.

Silicone-based products for scar management have been available for the past 30 years and have conventionally been recommended as the "gold standard" option for the prevention and treatment of hypertrophic scars and keloids. Silicones have been manufactured in various forms such as silicone sheets and more recently silicone gels.

Silicone sheets have to be worn over the scar for 12-24 hours each day for three to six months, or up to a year in some cases. The sheets can be used until they begin to disintegrate but most sheets are recommended by the manufactures to be washed daily with mild soap and water to prevent side effects such as rashes and infections. The composition of different silicone sheets varies widely, with some only containing medical grade silicone whereas others contain a combination of silicone and polytetra-fluoroethylene, which provides an internal reinforcement to create thin, durable sheeting and to increase flexibility and breathability. However, silicone sheets are neither suitable for use on large areas of skin nor on mobile body parts such as the joints. Furthermore, patients are reluctant to use the sheets on visible areas such as the face, and compliance with this treatment is therefore often an issue.

Due to the obvious problems with silicone sheets, many patients prefer to use silicone gels, especially on visible areas e.g. the face and/or hands. The gel is applied to the skin as a thin layer where it dries to form an adherent and flexible silicone layer/sheet that is impermeable to fluids. However it takes at least four to five minutes for the gel to dry on the skin, and the gel have to be applied at least twice a day for a recommended minimum treatment period of 60-90 days, in order for the patient to obtain the benefits of the treatment. Furthermore, the patient has to apply the gel using his/her finger, whereby the application procedure not only becomes messy, but there is also an obvious risk of contaminating the application site, e.g. a wound. Further problems with silicone gels are that they can stick to and discolour clothing during the drying period, and they have a tendency of being visible on the skin, since they leave a shining appearance on the area of which the gel has been applied. Thus, silicone gels are inconvenient to use, and many patients therefore have a tendency of either skipping one or more applications and/or stopping the treatment earlier than recommended, whereby the desired results are not achieved.

In recent years sticks comprising silicone have therefore been made available, in order to meet the demands for a higher patient compliance. An example of such a stick is e.g. disclosed in U.S. Pat. No. 8,557,287, and others are commercially available under trade names Prosil® and Remescar™ Scar stick. However, these known products contain a number of non-silicone components and thus have a relatively low silicone content, thereby not achieving the full beneficial effect of silicone on scar treatment. They also exhibit a low durability during normal use and need to be reapplied after e.g. exercise, washing or being out in the rain, in order to obtain the optimal benefits of the stick.

A further problem with the conventional silicone sticks, is that it has not been possible to manufacture a silicone stick, having both a high silicone concentration and a high sun protection factor (SPF). It is well known that scars are highly vulnerable to Ultraviolet light, and that the combination of inflammation in the healing tissue and sun exposure can lead to post-inflammatory hyperpigmentation (PIH), causing the scar and surrounding skin to turn dark brown. This discoloration can last months or even years. However, it has only been possible to manufacture the conventional silicone sticks e.g. Prosil® sport and Remescar™, with a SPF of 15, which is not considered sufficient by dermatologists to protect scars from UV-radiation.

Accordingly, there is a requirement to provide a new silicone composition which remedies the drawbacks of the prior art.

It is accordingly a first aspect of the present invention to provide a composition that can be used to treat skin injuries and/or minimize or eliminate scar formation.

It is a second aspect of the present invention to provide a composition which easily can be applied to the skin, which does not require any drying time, and which remains on the skin even after contact with water and/or sweat.

It is a third aspect of the present invention to provide a stick having a SPF that is higher than hitherto known for silicone sticks.

The present invention also provides a method for reducing or preventing scar formation, the method comprising applying the composition according to the invention to a skin area susceptible to scar formation. In one embodiment, the composition is applied to the skin area for a duration of at least a month, such as at least two months, more preferably 3-12 months. In one embodiment, the composition is applied to the skin area for a duration of up to 3 months, such as up to 6 months, more preferably up to 12 months. In one embodiment, the composition is applied to the skin area at least once daily for the entire duration of the method. The present invention also provides for a composition according to the invention for use in such a method. The present invention also provides for the use of a composition according to the invention for the manufacture of a cosmetic or pharmaceutical composition for use in such a method.

The present invention also provides a method for reducing or preventing post-inflammatory hyperpigmentation, the method comprising applying the composition comprising a sunscreen agent according to the invention to a skin area susceptible to post-inflammatory hyperpigmentation. In one embodiment, the composition is applied to the skin area for a duration of at least a month, such as at least two months, more preferably 3-12 months. In one embodiment, the composition is applied to the skin area for a duration of up to 3 months, such as up to 6 months, more preferably up to 12 months. In one embodiment, the composition is applied to the skin area at least once daily for the entire duration of the method. The present invention also provides for a composition comprising a sunscreen agent according to the invention for use in such a method. The present invention also provides for the use of a composition comprising a sunscreen agent according to the invention for the manufacture of a cosmetic or pharmaceutical composition for use in such a method.

These and further aspects are achieved according to the present invention by providing a composition comprising:
- a stearyl dimethicone,
- a C30-45 alkyl methicone, and
- a caprylyl methicone.

The combination of these three silicone compounds has proven to provide a unique effect by increasing hydration of stratum corneum and thereby facilitate regulation of fibroblast production and reduction in collagen production, whereby treatment of skin injuries is obtained, e.g. resulting in softer and flatter scar.

The silicone composition further protects the scarred tissue from bacterial invasion and therefore prevents bacteria-induced excessive collagen production in the scar tissue as well as reducing the itching and discomfort that sometimes are associated with scars. In addition, the provided silicone composition is substantially invisible after application, which significantly increases patient compliance.

The silicone composition preferably has a viscosity sufficient to provide the composition in the form of a stick, i.e. the silicone composition is provided as a firm, semisolid composition that substantially retains its shape when extruded from a dispenser, e.g. as known from lip balms/lip glosses or glue sticks. It is accordingly preferred that the silicone composition has a viscosity in the range of about 10 Pa·s (pascal seconds) to about 100 Pa·s (as measured by a Rheomat RM 80 at a shear rate of 200 s−1, and 20° C.), as this has proven to retain the compounds of the silicone composition in a uniform suspension or dispersion, prevent the silicone composition from leaking from the dispenser, and also ensures that the composition easily can be distributed/spread on the skin.

The dispenser for spreading the silicone composition according to the composition is preferably a conventional dispenser known e.g. form lip balm/lip gloss etc., preferably with an indicator providing a visual means for indicating the quantity of silicone composition remaining in the dispenser. Said visual indication may e.g. be obtained by providing a partly or completely transparent dispenser.

In embodiments where the silicone composition has a viscosity such that said composition is provided as a stick, this provides the advantages that the patient (by means of the dispenser) easily can apply a thin transparent silicone film on the desired area, thereby creating an optimal protective barrier for the scar to heal while maintaining the skins moisture balance. Furthermore, due to the high viscosity of the silicone composition, the composition neither requires any drying time, nor does it rub-off on e.g. the patient's cloth, thereby significantly improving patient compliance.

Stearyl dimethicone and C30-45 alkyl methicone are both alkyl-modified silicone waxes based on dimethyl silicones that have various amounts of methyl groups replaced with long-chain (C16 or higher) alkyl groups. The melting point of the respective alkyl-modified silicone wax depends on the degree of alkyl substitution, and the chain length of the hydrocarbon.

Stearyl dimethicone preferably has a melting point of about 32° C., which is about the temperature of the skin. Thus, when the silicone composition according to the invention comes into contact with the skin, the stearyl dimethicone will melt and provide a moisturizing effect. In order to ensure that a sufficient moisturizing effect is obtained, it is preferred that the silicone composition comprises at least 30 weight-% stearyl dimethicone, preferably at least 35 weight-% and even more preferred at least 40 weight-%, based on the total weight of the silicone composition according to the invention.

Stearyl dimethicones are known in the art, but a preferred stearyl dimethicone for use in the silicone composition according to the present invention is Dow Corning® 2503 Cosmetic Wax having the following general chemical formula:

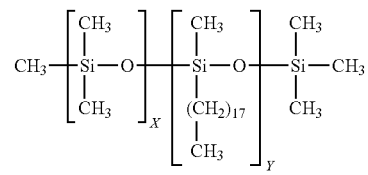

The C30-45 alkyl methicone preferably has a melting point above 50° C., preferably above 60° C. and even more preferably above or about 70° C., thereby providing sufficient integrity and adherence to the skin of the silicone composition at room temperature, i.e. between 18-25° C. When the silicone composition is provided in a substantially solid form e.g. in the form of a stick, it is preferred that the concentration of C30-45 alkyl methicone in the total silicone composition is at least 13 weight-%, preferably at least 15 weight-%, and even more preferred around 17 weight-% or even higher.

An example of a suitable C30-45 alkyl methicone is Dow Corning® AMS-C30 Cosmetic Wax having a general chemical formal of

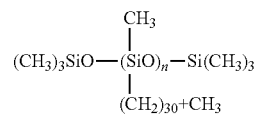

The third component caprylyl methicone, is a silicone fluid (at room temperature) and is added to the silicone composition for its occlusive properties, and for its ability to retain moisture on the surface of the skin. Caprylyl methicone is preferably added to the total silicone composition in an amount of at least 10 weight-%, preferably above 20 weight-%, but concentrations above 30 weight-% are also contemplated according to the invention.

An example of a suitable caprylyl methicone is Dow Corning® TI-2021 AMS Specialty Fluid, which has the following chemical formula:

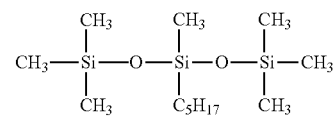

The composition according to the invention is intended for application on skin where the barrier functions of the skin may be impaired, such as recently damaged skin including scars and wounds, and it is thus desirable that the composition is free of compounds or agents that may serve as carbon or energy sources or other nutrients for microbes. In one embodiment, the composition is thus free of carbohydrates, such as sugars and starches, nucleotides, vitamins and provitamins, such as vitamins A, $B_1$, $B_2$, $B_3$, $B_5$, $B_6$, $B_7$, $B_9$, $B_{12}$, C, D, E and K.

In some embodiments, the composition according to the invention is free of cyclic polysiloxanes, such as cyclomethicone or cyclopentasiloxane.

Alternatively, the caprylyl methicone is substituted with cyclomethicone, i.e. cyclomethicone is added to the silicone composition according to the invention in the same concentrations as caprylyl methicone. Cyclomethicone is a clear, odourless silicone, that may assist in carrying oils into the top layer of the epidermis. However, cyclomethicone will evaporate relatively quickly when applied to the skin, and the use of cyclomethicone will therefore result in a silicone composition with a silky-smooth dry feel after application.

An example of a suitable cyclomethicone is Dow Corning® ST-20 Cyclomethicone 5-NF, which has the following chemical formula:

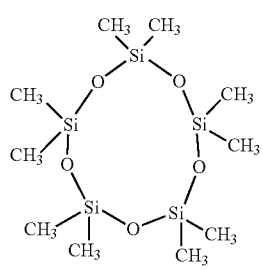

Since scars are highly vulnerable to UV, the silicone composition according to the invention may in a preferred embodiment comprises one or more sunscreen agents in a concentration such that the SPF of the silicone composition is at least 30 and even more preferred about 50, which is the SPF which is recommended by e.g. dermatologists in order to protect scars from UV-light.

Said one or more sunscreen agents may be any suitable agent capable of provide the desired effect. It is however preferred to use a physical sunscreen agent, i.e. an agent which contain mineral ingredients, such as titanium dioxide or zinc oxide, which work by being placed on top of the skin to deflect and scatter damaging UV rays away from the skin. In order to obtain an SPF of at least 30 (preferably 50) the concentration of the sunscreen agent in the final silicone composition is at least 20 weight-%, preferably at least 21 weight-% and even more preferred at least 22 weight-%. It is however preferred that the composition does not comprise more than 25 weight-% of the physical sunscreen agent.

An example of a suitable physical sunscreen agent containing zinc oxide is ZinClear® XP65COCO which is a 65 wt % dispersion of zinc oxide in coco-caprylate/caprate. Said product both offers the desired UV protection but also has an exceptional transparency, whereby the unacceptable whiteness on the skin, which sometimes is associated with physical sunscreen agents, effectively is prevented.

In one embodiment the silicone composition also comprises a small amount, below 1.0 weight-% of the final silicone composition, of one or more antioxidants and/or moisturizers. One preferred additional component in this respect is *camellia* oil e.g. *Camellia* Seed Oil. *Camellia* oil is not only known for being an excellent moisturizer but is also known to protects the skin from free radical damage due to its antioxidant characteristics. However, other similar compounds may also be incorporated into the silicone composition according to the invention. It is however preferred that the concentration of such one and more antioxidants and/moisturizers does not exceed 0.5 weight-% of the silicone composition, and preferably that the concentration of said one or more antioxidants and/moisturizers does not exceed 0.1 weight-% of the silicone composition.

In one preferred embodiment the three components of the composition, i.e. stearyl dimethicone, C30-45 alkyl methicone, and caprylyl methicone (or cyclomethicone) constitute at least 95% by weight of the total composition, preferably at least 99.5% by weight of the total composition, and even more preferred the entire composition.

The composition according to the invention can be manufactured conventionally by heating a mixture of a paste of the compounds of the silicone composition, at a temperature which is higher than the highest melting temperature of the waxes, and then cast the molten mixture in a mold. This process makes it possible to obtain a composition in a solid form, i.e., in the form of a stick or of a small dish.

An example of a first preferred composition (without sun protection) is provided in table 1:

TABLE 1

| Compound | Quantity (weight-% of total composition) |
| --- | --- |
| Stearyl dimethicone (Dow Corning ® 2503 Cosmetic Wax) | 47.5 |
| C30-45 alkyl methicone (Dow Corning ® AMS-C30 Cosmetic Wax) | 17.5 |
| Caprylyl methicone (Dow Corning ® TI-2021 AMS Specialty Fluid) | 34.5 |
| Camellia oil | 0.5 |

The first preferred composition has a viscosity of about 60 Pa·s (pascal seconds) (as measured by a Rheomat RM 80 at a shear rate of 200 s−1, and 20° C.), thereby providing a semisolid but firm composition which can be arranged as a stick, e.g. in a suitable dispenser.

An example of a second preferred silicone composition with an SPF of 50 is provided in table 2:

TABLE 2

| Compound | Quantity (weight-% of total composition) |
| --- | --- |
| ZinClear ® XP65COCO (Sunscreen agent) | 32 weight-% ZinClear ® XP65COCO, i.e. the final silicone composition contains 21 weight - % zinc oxide and 11 weight-% coco-caprylate/caprate. |
| Stearyl dimethicone (Dow Corning ® 2503 Cosmetic Wax) | 40.5 |
| C30-45 alkyl methicone (Dow Corning ® AMS-C30 Cosmetic Wax) | 16.9 |
| Caprylyl methicone (Dow Corning ® TI-2021 AMS Specialty Fluid) | 11 |
| Camellia oil | 0.1 |

The silicone composition in table 2 has a viscosity of about 58 Pa·s (pascal seconds) (as measured by a Rheomat RM 80 at a shear rate of 200 s−1, and 20° C.), thereby providing a semisolid but firm composition which can be arranged as a stick, e.g. in a suitable dispenser.

The advantages of silicone sticks having compositions as disclosed e.g. in table 1 and table 2, include easy administration, since they can be applied as a thin transparent silicone film on a desired skin area, e.g. on irregular skin or scar surfaces, the face, hands, moving parts (joints and flexures) and they can be applied to all scar sizes.

Furthermore, said silicone compositions do not require any drying time, have an improved adherence to the patient's skin, i.e. the compositions do not rub-off on e.g. the patient's cloth, and the compositions have proven to be more resistant to water/sweet than hitherto known. Test have for instance shown that in contrast to the commercially available silicone sticks, the compositions in table 1 and table 2 will repel water, creating small water droplets on the silicone film which thereafter glides away. This effectively means that the applied silicone film will not erode/be removed if the patient is e.g. sweating during exercise or is in a hot climate, and/or when the patient is washing his/her hands.

In addition, the silicone composition of the invention makes it possible to obtain a film which is homogeneous, which spreads easily and uniformly, and which is substantially invisible, while providing an optimal protective barrier for a scar to heal. The film obtained also has a light texture and remains comfortable and can be worn throughout the day.

Thus, the use of the silicone composition according to the invention, e.g. disclosed in table 1 and 2, exhibit improved wearability, substantivity, and durability, and will therefore significantly improve patient compliance. The patient only has to apply a protective silicone film on the scar, a few times a day, e.g. morning and evening, in order to create an optimal healing environment for the scar while maintaining the skins moisture balance.

Modifications and combinations of the above principles and compounds are foreseen within the scope of the present invention. The examples are provided for illustration of the invention and shall not be construed as limiting the scope of the invention, which is that of the appended claims.

All words and terms used in the present disclosure shall be construed as having the meaning generally given to them by the person of ordinary skill in the art. The term "silicone composition" refers to a composition comprising at least one silicone compound, i.e. a synthetic compound made up of repeating units of siloxane. Any composition comprising at least one silicone compound is, in the context of the present disclosure, a "silicone composition".

The following embodiments are specifically contemplated
1. A composition comprising:
   a stearyl dimethicone,
   a C30-45 alkyl methicone, and
   a caprylyl methicone.
2. The composition according to embodiment 1, wherein the composition has a viscosity sufficient to provide said composition in the form of a stick.
3. The composition according to embodiment 1 or 2, wherein the composition has a viscosity in the range of about 10 Pa·s (pascal seconds) to about 100 Pa·s (as measured by a Rheomat RM 80 at a shear rate of 200 s−1, and 20° C.).
4. The composition according to embodiment 1, 2 or 3 wherein the stearyl dimethicone has a melting point of about 32° C.
5. The composition according to any one of the preceding embodiments, wherein the composition comprises at least 30 weight-% stearyl dimethicone, preferably at least 35 weight-% stearyl dimethicone and even more preferred at least 40 weight-% stearyl dimethicone, based on the total weight of the composition.
6. The composition according to any one of the preceding embodiments, wherein the C30-45 alkyl methicone has a melting point above 50° C., preferably above 60° C. and even more preferably above or about 70° C.
7. The composition according to any one of the preceding embodiments, wherein the composition comprises at least 13 weight-% C30-45 alkyl methicone, preferably at least 15 weight-% C30-45 alkyl methicone, and even more preferably around or above 17 weight-% C30-45 alkyl methicone, based on the total weight of the composition.
8. The composition according to any one of the preceding embodiments, wherein the composition comprises at least 10 weight-% caprylyl methicone, preferably at least 20 weight-% caprylyl methicone, and even more preferred at least 30 weight-% caprylyl methicone, based on the total weight of the composition.
9. The composition according to any one of the preceding embodiments, wherein said composition further comprises one or more antioxidants and/or moisturizers in an amount not exceeding 1.0 weight-% of the composition, preferably not exceeding 0.5 weight-% of the composition.
10. The composition according to any one of the preceding embodiments, wherein said composition further comprises one or more sunscreen agents in a concentration such that the Sun Protection Factor (SPF) of the composition is at least 30 and even more preferred about 50.
11. The composition according to embodiment 10, wherein the concentration of the sunscreen agent is at least 20 weight-%, preferably at least 21 weight-% and even more preferred around or above 22 weight-%, based on the total weight of the composition.
12. The composition according to embodiment 10 or 11 wherein the sunscreen agent is a physical sunscreen agent containing mineral ingredients, such as titanium dioxide or zinc oxide.
13. The composition according to any one of the embodiments 1-9, containing 47.5 weight-% stearyl dimethicone, 17.5 weight-% C30-45 alkyl methicone, 34.5 weight-% caprylyl methicone and 0.5 weight-% *camellia* oil, based on the total weight of the composition.
14. The composition according to any one of the embodiments 10-12, containing 21 weight-% zinc oxide, 11 weight-% coco-caprylate/caprate, 40 weight-% stearyl dimethicone, 16.9 weight-% C30-45 alkyl methicone, 11 weight-% caprylyl methicone and 0.1 weight-% *camellia* oil, based on the total weight of the composition.
15. A stick comprising the composition according to any one of the embodiments 1 to 12 or consisting of the composition according to embodiment 13 or 14.
16. Use of the composition according to any of the embodiments 1-14 or the stick according to embodiment 15, for applying a thin transparent silicone film on a desired skin area, e.g. on irregular skin or scar surfaces.
17. A method for reducing or preventing scar formation, the method comprising applying the composition according to any one of embodiments 1-14 to a skin area susceptible to scar formation.
18. A method for reducing or preventing post-inflammatory hyperpigmentation, the method comprising applying the composition according to any one of embodiments 10-12 or 14 to a skin area susceptible to post-inflammatory hyperpigmentation.
19. The method according to embodiment 17 or 18, wherein the composition is applied at least one time per day.

The invention claimed is:
1. A composition comprising:
   a stearyl dimethicone,
   a C30-45 alkyl methicone,
   at least 20 weight-% caprylyl methicone based on the total weight of the composition, and
   at least 20 weight-% of one or more sunscreen agents such that the Sun Protection Factor (SPF) of the composition is at least 30, wherein the composition is in the form of a stick and has a viscosity in the range of about 10 Pa·s (pascal seconds) to about 100 Pa·s, as measured by a Rheomat RM 80 at a shear rate of 200 s−1, and 20° C.

2. The composition according to claim 1 wherein the stearyl dimethicone has a melting point of about 32° C.

3. The composition according to claim 1, wherein the composition comprises at least 30 weight-% stearyl dimethicone, based on the total weight of the composition.

4. The composition according to claim 1, wherein the C30-45 alkyl methicone has a melting point above 50° C.

5. The composition according to claim 1, wherein the composition comprises at least 13 weight-% C30-45 alkyl methicone, based on the total weight of the composition.

6. The composition according to claim 1, wherein said composition further comprises one or more antioxidants and/or moisturizers in an amount not exceeding 1.0 weight-% of the composition.

7. The composition according to claim 1, wherein said composition further comprises one or more sunscreen agents in a concentration such that the Sun Protection Factor (SPF) of the composition is at least 50.

8. The composition according to claim 7, wherein the sunscreen agent is a physical sunscreen agent comprising a mineral ingredient.

9. The composition according to claim 1, wherein the composition comprises at least 35 weight-% stearyl dimethicone based on the total weight of the composition.

10. The composition according to claim 1, wherein the C30-45 alkyl methicone has a melting point above 60° C.

11. The composition according to claim 1, wherein the composition comprises at least 15 weight-% C30-45 alkyl methicone, based on the total weight of the composition.

12. The composition according to claim 1, wherein the composition comprises at least 30 weight-% caprylyl methicone, based on the total weight of the composition.

13. The composition according to claim 1, containing 47.5 weight-% stearyl dimethicone, 17.5 weight-% C30-45 alkyl methicone, 34.5 weight-% caprylyl methicone and 0.5 weight-% *camellia* oil, based on the total weight of the composition.

14. A method for reducing scar formation, the method comprising applying the composition of claim 1 to a skin area susceptible to scar formation.

15. The method according to claim 14, wherein the stearyl dimethicone has a melting point of about 32° C.

16. The method according to claim 14, wherein the composition comprises at least 30 weight-% stearyl dimethicone, based on the total weight of the composition.

17. The method according to claim 14, wherein the C30-45 alkyl methicone has a melting point above 50° C.

18. The method according to claim 14, wherein the composition comprises at least 13 weight-% C30-45 alkyl methicone, based on the total weight of the composition.

19. The method according to claim 14, wherein said composition further comprises one or more antioxidants and/or moisturizers in an amount not exceeding 1.0 weight-% of the composition.

20. The method according to claim 14, wherein said composition further comprises one or more sunscreen agents in a concentration such that the Sun Protection Factor (SPF) of the composition is at least about 50.

21. The method according to claim 14, wherein the sunscreen agent is a physical sunscreen agent comprising a mineral ingredient.

22. The method according to claim 14, wherein the composition is applied to the skin at least one time per day for at least one month.

23. The method according to claim 14, wherein the composition contains 47.5 weight-% stearyl dimethicone, 17.5 weight-% C30-45 alkyl methicone, 34.5 weight-% caprylyl methicone and 0.5 weight-% *camellia* oil, based on the total weight of the composition.

24. The method according to claim 23, wherein the concentration of the sunscreen agent is at least 22 weight-%, based on the total weight of the composition.

25. A method for reducing post-inflammatory hyperpigmentation, the method comprising applying the composition of claim 1 to a skin area susceptible to post-inflammatory hyperpigmentation.

26. The method according to claim 25, wherein the one or more sunscreen agents in the composition of claim 1 is is a physical sunscreen agent comprising a mineral ingredient.

27. The method according to claim 25, wherein the composition is applied to the skin at least one time per day for at least one month.

28. The method according to claim 25, wherein the concentration of the one or more sunscreen agents in the composition of claim 1 is at least 22 weight-%, based on the total weight of the composition.

29. A method of treating skin comprising applying the composition according to claim 1 to skin.

* * * * *